(12) United States Patent
Matsuda et al.

(10) Patent No.: US 11,731,177 B2
(45) Date of Patent: Aug. 22, 2023

(54) USED PAPER DIAPER PROCESSING APPARATUS

(71) Applicant: Panasonic Corporation, Osaka (JP)

(72) Inventors: Genichiro Matsuda, Nara (JP);
Hidenao Kataoka, Osaka (JP);
Naofumi Hino, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 520 days.

(21) Appl. No.: 17/024,025

(22) Filed: Sep. 17, 2020

(65) Prior Publication Data

US 2021/0086242 A1    Mar. 25, 2021

(30) Foreign Application Priority Data

Sep. 19, 2019    (JP) ................................ 2019-169943

(51) Int. Cl.
| | |
|---|---|
| *B09B 5/00* | (2006.01) |
| *B09B 3/80* | (2022.01) |
| *A61L 2/00* | (2006.01) |
| *A61L 2/16* | (2006.01) |
| *A61L 2/18* | (2006.01) |

(Continued)

(52) U.S. Cl.
CPC ................. *B09B 3/80* (2022.01); *A61L 2/00* (2013.01); *A61L 2/16* (2013.01); *A61L 2/18* (2013.01); *B03B 7/00* (2013.01); *B08B 13/00* (2013.01); *B09B 3/00* (2013.01); *B09B 5/00* (2013.01); *B09B 2101/02* (2022.01)

(58) Field of Classification Search
CPC .... A61L 2/00; B03B 7/00; B09B 3/00; B02C 17/002; B02C 17/007; B02C 17/02
See application file for complete search history.

(56) References Cited

U.S. PATENT DOCUMENTS 5,268,105 A    12/1993    Uejima et al.
6,478,724 B1    11/2002    Beattey
(Continued)

FOREIGN PATENT DOCUMENTS

CN    1518481    8/2004
CN    1899715    1/2007
(Continued)

OTHER PUBLICATIONS

Extended European Search Report dated May 10, 2021 in European Application No. 20209962.8.
(Continued)

*Primary Examiner* — Sean E Conley
*Assistant Examiner* — Justin Hwang
(74) *Attorney, Agent, or Firm* — Wenderoth, Lind & Ponack, L.L.P.

(57) ABSTRACT

The peeling member is disposed inside the inner tank. The switching mechanism is provided for switching between the state of rotating the peeling member in the interlocking manner with the inner tank and the state of being disconnected the peeling member from the inner tank. With the peeling member disconnected from the inner tank, one of them is rotated, the used paper diaper stored is peeled off from the inner surface of the inner tank, and then, the used paper diaper processed in the processing tank is discharged from the bottom of the processing tank to the take-out unit via the opening and closing unit.

4 Claims, 10 Drawing Sheets

(51) Int. Cl.
  *B09B 3/00*  (2022.01)
  *B08B 13/00* (2006.01)
  *B03B 7/00*  (2006.01)
  *B09B 101/02* (2022.01)

(56) References Cited

U.S. PATENT DOCUMENTS

| | | | |
|---|---|---|---|
| 10,066,331 | B2 | 9/2018 | Hendrickson et al. |
| 2003/0019961 | A1 | 1/2003 | Holmen et al. |
| 2004/0209753 | A1* | 10/2004 | Kikushima ............ D21B 1/322 492/37 |
| 2015/0265737 | A1 | 9/2015 | Yamaguchi et al. |
| 2020/0087828 | A1 | 3/2020 | White et al. |
| 2020/0269292 | A1 | 8/2020 | Matsuda et al. |

FOREIGN PATENT DOCUMENTS

| | | |
|---|---|---|
| CN | 104582866 | 4/2015 |
| CN | 109290279 | 2/2019 |
| EP | 0 378 927 | 7/1990 |
| EP | 0 545 520 | 6/1993 |
| EP | 1 415 733 | 5/2004 |
| EP | 3 237 665 | 11/2017 |
| JP | 5-154188 | 6/1993 |
| JP | 6-269746 | 9/1994 |
| JP | 7-291405 | 11/1995 |
| JP | 8-168587 | 7/1996 |
| JP | 2001-104929 | 4/2001 |
| JP | 2002-292304 | 10/2002 |
| JP | 2003-19169 | 1/2003 |
| JP | 2003-190928 | 7/2003 |
| JP | 2004-514557 | 5/2004 |
| JP | 3840383 | 11/2006 |
| JP | 3895081 | 3/2007 |
| JP | 2008-35925 | 2/2008 |
| JP | 2008-307445 | 12/2008 |
| JP | 2010-84031 | 4/2010 |
| JP | 4685973 | 5/2011 |
| JP | 2012-81433 | 4/2012 |
| JP | 2012-225516 | 11/2012 |
| JP | 2013-236989 | 11/2013 |
| JP | 2014-155903 | 8/2014 |
| JP | 2018-167153 | 11/2018 |
| JP | 2019-81131 | 5/2019 |
| JP | 2019-136662 | 8/2019 |
| JP | 2019-206656 | 12/2019 |
| JP | 2020-131157 | 8/2020 |
| KR | 2003-0017286 | 3/2003 |
| RU | 2 105 593 | 2/1998 |
| WO | 94/20668 | 9/1994 |
| WO | 02/072271 | 9/2002 |
| WO | 2013/144336 | 10/2013 |

OTHER PUBLICATIONS

Office Action dated Dec. 16, 2022 in Chinese Patent Application No. 202010991823.0, with English-language translation.
Notification of Reasons for Refusal dated May 25, 2021 in Japanese Application No. 2019-031505 with English translation.
Extended European Search Report dated Jun. 17, 2021 in European Application No. 21150076.4.
Notification of Reasons for Refusal dated Jun. 21, 2022 in Japanese Application No. 2020-007638 with English translation thereof.
Notification of Reasons for Refusal dated May 27, 2022 in Chinese Application No. 202010991823.0 with English translation thereof.
Office Action and Search Report dated Jun. 17, 2022 in corresponding Chinese Patent Application No. 202110072028.6, with English translation.
Office Action dated Jun. 3, 2022 in U.S. Appl. No. 16/794,970.
Extended European Search Report dated Feb. 17, 2021 in European Application No. 20196180.2.
Notification of Reasons for Refusal dated Apr. 5, 2022 in Japanese Patent Application No. 2019-169943, with English-language translation.
Office Action dated Nov. 18, 2022 in U.S. Appl. No. 16/794,970.
Chinese Office Action including Chinese Search Report dated Oct. 27, 2021 in corresponding Chinese Patent Application No. 202010105696.X with Partial English translation of Chinese Office Action and Full English translation of the Chinese Search Report.
Office Action dated Dec. 7, 2022 in corresponding U.S. Appl. No. 17/144,311.
Extended European Search Report dated Jul. 10, 2020 in European Application No. 20158456.2.
Office Action dated Apr. 24, 2023 in corresponding U.S. Appl. No. 17/144,311.

* cited by examiner

USED PAPER DIAPER PROCESSING APPARATUS

BACKGROUND OF THE INVENTION

Field of the Invention

The present disclosure relates to a used paper diaper processing apparatus that reduces weight by removing water from a superabsorbent polymer contained in a used paper diaper.

More specifically, the present disclosure relates to a used paper diaper processing apparatus in which a water absorption function of a superabsorbent polymer that absorbs water contained in excrement is lowered and water is removed by mixing the superabsorbent polymer and a chemical containing divalent metal ions or the like, and in which weight is reduced by dehydration after an amount of water contained in a used paper diaper is lowered.

Description of the Related Art

Since a used paper diaper contains a large amount of water, when a large amount of used paper diapers is handled in a nursing home etc., weight of the paper diapers may be an issue. The paper diaper contains a superabsorbent polymer and can hold a large amount of water. Moreover, once the water has been absorbed by the superabsorbent polymer, it is difficult to remove the water as it is.

Therefore, a used paper diaper processing apparatus has been proposed in which a used paper diaper soaked in water is separated and disassembled into a water-soluble substance and an insoluble substance, and the separated and disassembled water-soluble substance is discharged to a sewage processing facility along with sewage, thereby reducing weight, and volume of the paper diaper (see Patent Document 1).

Figure 7A:
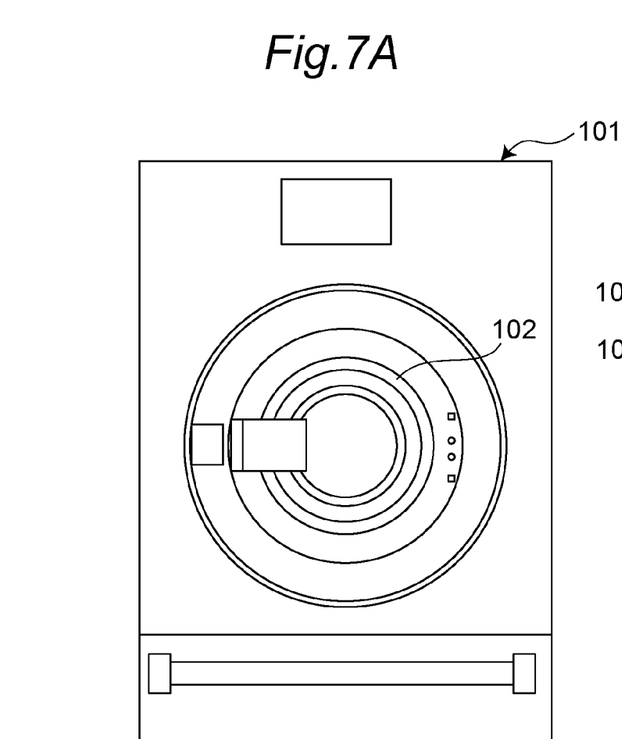
FIGS. 7A and 7B are sectional views of a conventional used paper diaper processing apparatus.
Figure 7B:
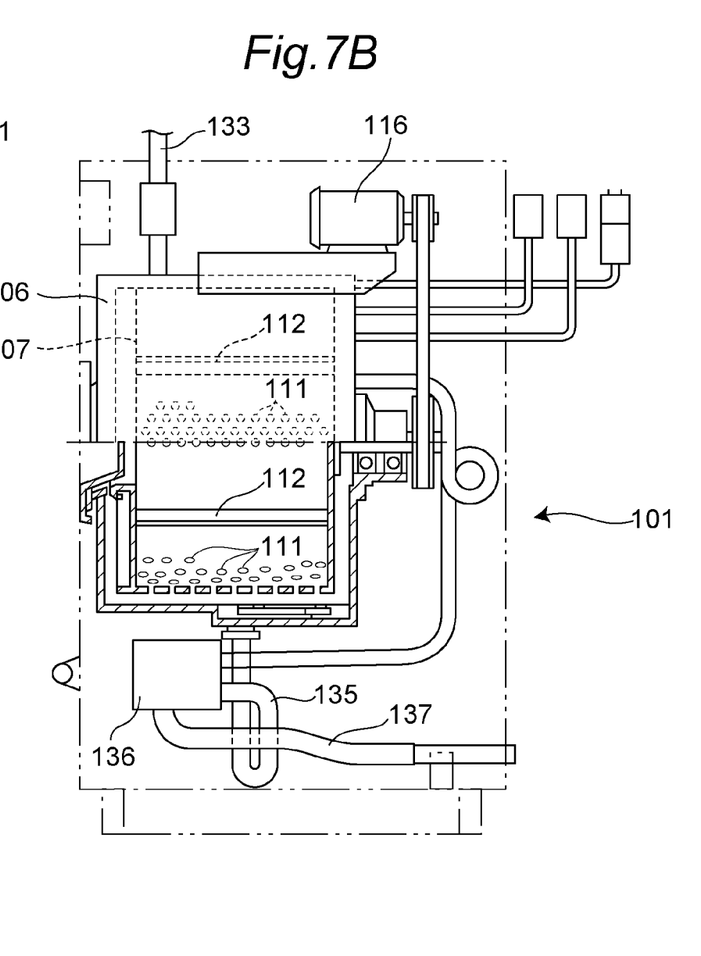

FIGS. 7A and 7B show an example of a conventional used paper diaper processing apparatus 101 described in Patent Document 1. FIG. 1A is a front view of the conventional used paper diaper processing apparatus 101, and FIG. 7B shows a side view thereof. In FIGS. 7A and 7B, 102 indicates an opening/closing lid, 106 indicates an outer drum, 107 indicates a rotating drum, 111 indicates a through hole, 112 indicates a stirring protrusion, 116 indicates a motor, 133 indicates a water supply pipe, 135 and 137 indicate discharge pipes, and 136 indicates an opening/closing valve.

Next, operation of the conventional used paper diaper processing apparatus 101 will be described.

A used paper diaper is put into the rotating drum 107 through the opening/closing lid 102 that is opened.

Next, after a predetermined amount of water (that is, amount by which a lower portion of the rotating drum 107 is immersed) is supplied from the water supply pipe 133 into the outer drum 106, the motor 116 is started to rotate the rotating drum 107, and a water flow is generated inside the rotating drum 107. As a result, the paper diaper in the rotating drum 107 can be separated and disassembled while being immersed in the water. At this time, because of the stirring protrusions 112, stirring processing of the paper diaper is promoted, and separation and disassembling processing is promoted. The separated and disassembled paper diaper passes through the discharge pipes 135 and 137 via the through holes ill and is drained to a sewer pipe connected to the sewage processing facility.

However, in the used paper diaper processing apparatus 101 described in Patent Document 1, the paper diaper is separated and disassembled in a processing step, and a fiber component, of the disassembled paper diaper is directly discharged to the sewage processing facility. Accordingly, there is an issue in which a load for processing the fiber component of the disassembled paper diaper increases in wastewater processing in the sewage processing facility. Therefore, upon discharging to the sewer pipe, it is necessary to introduce an apparatus for removing the fiber component of the disassembled paper diaper by a filter.

Therefore, as another processing system, a used paper diaper processing apparatus has been proposed in which water is removed from a superabsorbent polymer by reacting with a chemical containing divalent metal ions or the like, thereby reducing weight of a paper diaper (see Patent Document 2).

FIGS. 8A-8D shows an example of a conventional used paper diaper processing apparatus 201 described in Patent Document 2. In FIGS. 8A-8D, 202 indicates lime, 203 indicates hypochiorous acid, 204 indicates a processing tank, 205 indicates a used paper diaper, 206 indicates water, 207 indicates a liquid, and 208 indicates wastewater.

Subsequently, operation of the conventional used paper diaper processing apparatus 201 will be described.

Figure 8A:
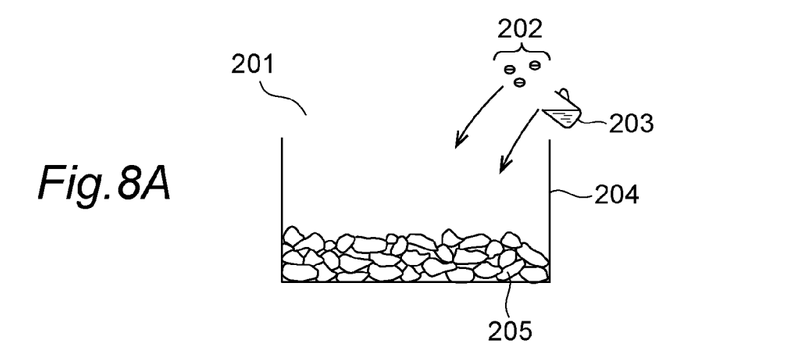
FIGS. 8A-8D are sectional views of a conventional used paper diaper processing apparatus.

First, as shown in FIG. 8A, the lime 202, the hypochiorous acid 203, and the used paper diaper 205 are put into the processing tank 204.

Figure 8B:
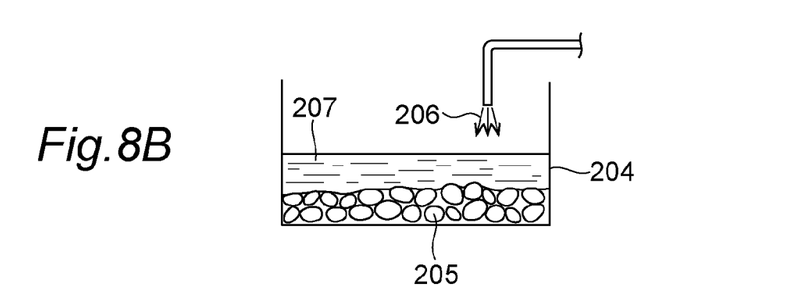
Figure 8C:
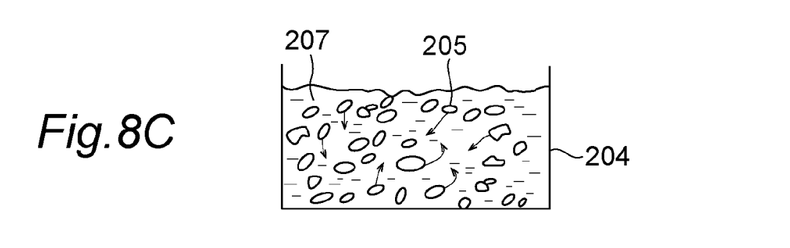

Next, as shown in FIGS. 8B and 8C, the water 206 is put into the processing tank 204 so that stirring is possible, and then the stirring is performed for a predetermined time. When the stirring is continued in this state, Ca ions contained in the lime react with the superabsorbent polymer of the paper diaper, and water contained in the superabsorbent polymer is removed.

Figure 8D:
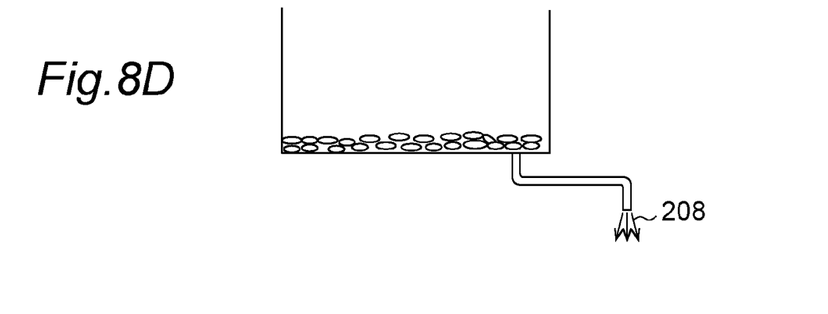

Finally, as shown in FIG. 8D, the liquid 207 in the processing tank 204 is discharged out of the processing tank 204 and dehydrated, and then the wastewater 208 is discharged.

PRIOR ART DOCUMENTS

Patent Documents

Patent Document 1: Japanese Patent Laid-open Publication No. 2001-104929
Patent Document 2: Japanese Patent Laid-open Publication No. 2010-84031

However, in the used paper diaper processing apparatus 201 described in Patent Document 2, dehydration processing is performed after the water contained in the superabsorbent polymer is removed in the processing tank 204, and only the paper diaper remains in the processing tank 204. In order to take out the remaining used paper diaper, it is necessary for an operator to take it out from above. Also, it is necessary for the operator to place the taken-out used paper diaper into a disposal bag such as a plastic bag. Accordingly, there is an issue in which work and hygiene burdens are forced on the operator.

SUMMARY OF THE INVENTION

In view of such points, an object of the present disclosure is to provide a used paper diaper processing apparatus, in which, by reducing the weight without separating arid disassembling the paper diaper and by implementing a series of operations up to taking-out operation of the used paper diaper after the processing in the processing apparatus, work and hygiene burdens on an operator at a nursing home and the like are reduced without increasing a burden of wastewater processing in a sewage processing facility.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature; a used paper diaper processing apparatus, comprising:

a processing tank that processes a used paper diaper;

a liquid supply unit that supplies a processing liquid to the processing tank;

a liquid discharge unit that discharges the processing liquid from the processing tank; and a take-out unit that takes out a paper diaper processed in the processing tank below the processing tank, wherein the processing tank has:

an inner tank having a Cylindrical shape that stores the used paper diaper and has a plurality of through holes smaller than the paper diaper on at least either a side surface thereof or a bottom surface thereof, and an outer tank that surrounds the side surface and the bottom surface of the inner tank;

at least one peeling member inside the inner tank;

a switching mechanism that performs switching between a state in which the peeling member and the inner tank rotate in an interlocking manner and a state in which the peeling member is disconnected from the inner tank, the used paper diaper processing apparatus further comprising:

a rotation drive unit that rotates the inner tank or the peeling member around an axis of the inner tank; and an opening and closing unit that discharges the paper diaper processed in the processing tank from a bottom of the processing tank to the take-out unit.

According to the used paper diaper processing apparatus according to the above aspect of the present disclosure, the bottom of the outer tank and the bottom of the inner tank can be opened and closed, the peeling member is included which is installed inside the inner tank and for which switching can be performed between a state of rotating in an interlocking manner with the inner tank and a state of being disconnected from the inner tank, the disconnected peeling member peels off the diaper after dehydration from the side surface of the inner tank so that the diaper after processing can be dropped and taken out from below, and it is possible to reduce work and hygiene burdens of an operator.

BRIEF DESCRIPTION OF THE DRAWINGS

These and other aspects and features of the present invention will become clear from the following description taken in conjunction with the embodiments thereof with reference to the accompanying drawings, in which.

DETAILED DESCRIPTION

First Embodiment

Hereinafter, a used paper diaper processing apparatus 1 according to an embodiment of the present disclosure will be described in detail with reference to the drawings. In the drawings, the same or corresponding parts are denoted by the same reference numerals and description thereof will not be repeated. Note that, in order to make the explanation easy to understand, a configuration is shown in a simplified or schematic manner or some constituent members are omitted in the drawings referred to below. Further, a dimensional ratio between the constituent members shown in each drawing does not necessarily indicate an actual dimensional ratio.

[Overall Configuration]

Figure 1A:
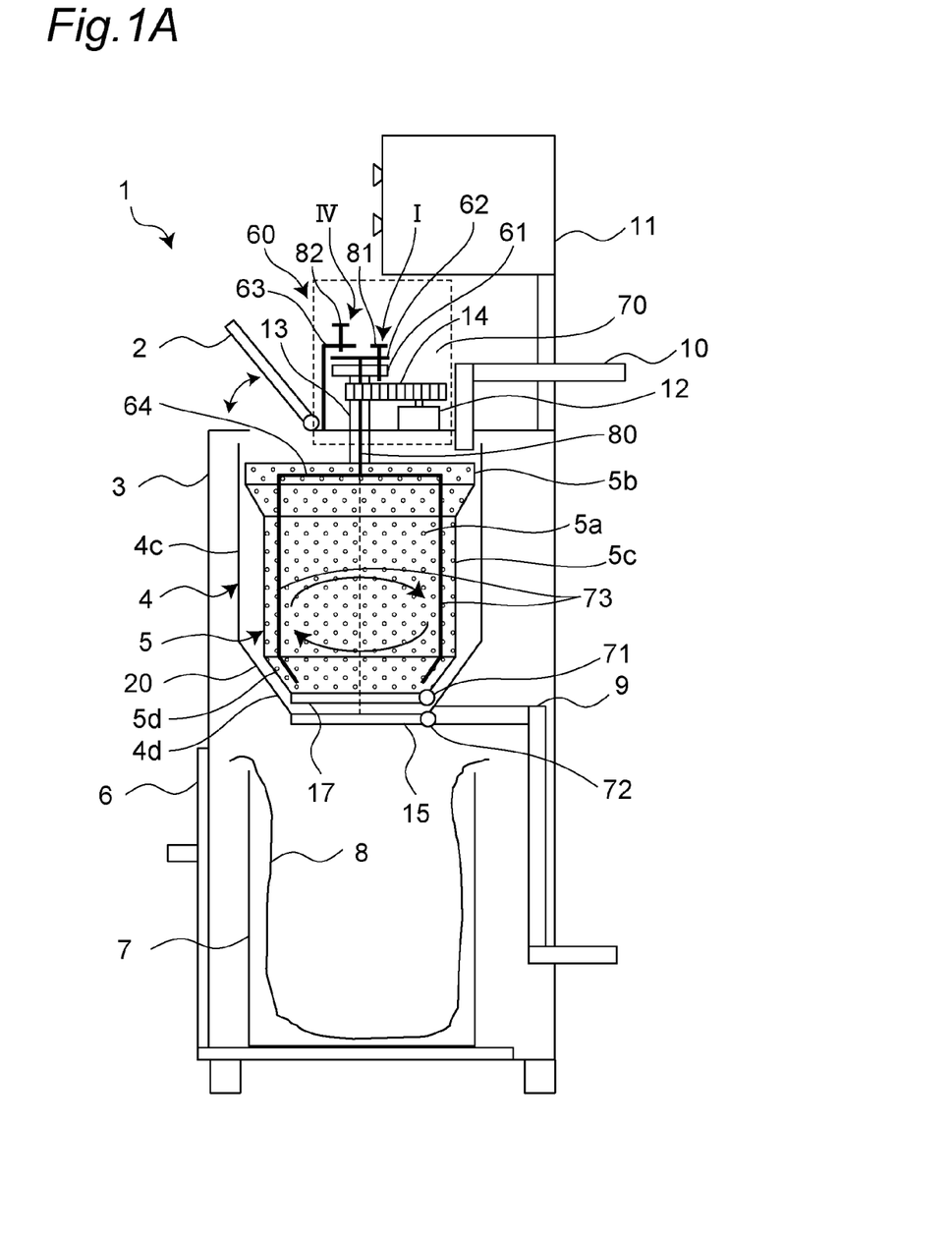
FIG. 1A is a side sectional view showing a configuration of a used paper diaper processing apparatus according to a first embodiment of the present disclosure.

First, an overall configuration of the used paper diaper processing apparatus 1 will be described. FIG. 1A is a side sectional view showing a configuration of the used paper diaper processing apparatus 1 according to the first embodiment of the present disclosure.

The used paper diaper processing apparatus 1 includes at least a processing tank 20, a liquid supply unit 10, a liquid discharge unit 9, and a take-out unit 6. More specifically, the used paper diaper processing apparatus 1 further includes a loading door 2, an apparatus main body 3, a storage container 7, a disposal bag 8, a control apparatus 11, and a rotation drive unit 70.

The processing tank 20 for processing a used paper diaper is disposed in an upper portion of the apparatus main body 3, and composed of, for example, a cylindrical outer tank 4 and a cylindrical inner tank 5. The inner tank 5 is disposed in the outer tank 4.

An upper portion of the inner tank 5 is a conical portion 5b on an upper side configured as a wide opening that allows easy entry of a used paper diaper 18, a middle portion thereof is a cylindrical portion 5c continued to the conical portion 5b on the upper side, and a lower portion thereof is a tapered portion 5d having a conical shape narrowing toward a bottom surface thereof from the cylindrical portion 5c.

A part, extending from an upper portion and a middle portion of the outer tank 4 is a cylindrical portion 4c, and a lower portion thereof is, in the same manner as the tapered portion 5d having a conical shape, a tapered portion 4d having a conical shape narrowing toward a bottom surface thereof from the cylindrical portion 4c.

Inside the inner tank 5, two sticks 73 hanging downward having, for example, a quadrangular cross-section are attached in symmetrical positions with respect to a rotation axis of the inner tank 5 (for example, positions having 180° intervals) as an example of the peeling member. Upper ends of these two sticks 73 are connected by a connecting stick 64, which is disposed along a radial direction of the rotation axis. A central part, of the connecting stick 64 is connected to a connecting shaft 80. The sticks 73 are configured so as to be switched between a state of rotating in art interlocking manner with the inner tank 5 and a state of being disconnected from the inner tank 5 by a switching mechanism 60. The switching mechanism 60 will be described after a description of the inner tank 5.

Note that the cross-sectional shape of the sticks 73 is not limited to quadrangle, and may be a triangular or rhombic stick or a plate member. A material for the sticks 73 may be rigid enough to peel a diaper off from the inner tank 5, and a metal such as stainless steal (SUS) is exemplified.

The loading door 2 is attached to an upper portion of the apparatus main body 3 so as to be openable and closable. The used paper diaper 18 is put into the inner tank 5 after the loading door 2 is opened.

The outer tank 4 is a container that can store water. Water can be stored through introduction of water from the liquid supply unit 10 into the processing tank 20, and a chemical can also be introduced from the liquid supply unit 10 into the processing tank 20. As a result, a processing liquid 19 can be supplied from the liquid supply unit 10 into the processing tank 20. Note that, as will be described in detail later, a processing liquid 19 in which water and a chemical are mixed can also be supplied from the liquid supply unit 10 into the processing tank 20.

Further, the liquid in the outer tank 4 is discharged to the outside using the liquid discharge unit 9. Inside the outer tank 4, the cylindrical inner tank 5 having a plurality of through holes 5a on at least either a side surface or a bottom surface is disposed. Each of the through holes 5a is smaller than the used paper diaper 18 so that the used paper diaper 18 does not fall off from the through holes 5a.

Further, the inner tank 5 is rotatably connected to the rotation drive unit 70. The rotation drive unit 70 is driven under the control of the control apparatus 11. As an example, the rotation drive unit 70 is composed of a shaft 13 fixed to the inner tank 5 along the rotation axis of the inner tank 5, a belt 14 that engages with the shaft 13 and rotates the shaft 13, and a motor 12 having a rotating shaft to which a gear engaging with the belt 14 is fixed. As a result, under the control of the control apparatus 11, the inner tank 5 can be rotated with respect to the outer tank 4 by driving of the motor 12. As an example, the rotation axis of the inner tank 5 can be disposed along a vertical direction.

The shaft 13 is a cylindrical member, and the connecting shaft 80 of the sticks 73 penetrates through a through hole in a center portion of the shaft 13 in such a manner as to freely rotatable around the rotation axis. FIG. 1A shows a perspective view of the above. An upper portion of the shaft 13 is provided with the switching mechanism 60.

As an example, the switching mechanism 60 includes at least an inner tank connecting pin 81 as an example of a first connecting member, and a main body connecting pin 82 as an example of a second connecting member. In order to perform connection switching smoothly, the switching mechanism 60 preferably further includes a first circular plate 61 for connection switching connected to the inner tank 5, and a second circular plate 62 for connection switching connected to the sticks 73. These circular plates each function as a connecting member, and a shape thereof is not limited to a circular plate.

A center portion of the first circular plate 61 is fixed to an upper end of the shaft 13 of the inner tank 5, and the first circular plate 61 always rotates integrally with the shaft 13. The connecting shaft 80 of the sticks 73 passes through the shaft 13, penetrates upward through an opening in the center portion of the first circular plate 61, and is exposed.

A center portion of the second circular plate 62 is fixed to a portion, above the first circular plate 61, at an upper end of the connecting shaft 80 of the sticks 73 that penetrates through the first circular plate 61 and is exposed, and the second circular plate 62 always rotates integrally with the connecting shaft 80.

The inner tank connecting pin 81 is disposed in an outer circumferential portion of the second circular plate 62 so as to penetrate therethrough in a thickness direction, that is, a vertical direction, supported in an erected manner on the second circular plate 62, arid can engage with or penetrate through (simply referred to as "penetrate" hereinafter) the first circular plate 61 after penetrating through the second circular plate 62. As a result, the inner tank connecting pin 81 can move between a connecting position I and a disconnecting position II through, for example, extraction and insertion in the vertical direction, where in the connecting position I, the inner tank connecting pin 81 connects the sticks 73 to the inner tank 5 so that the sticks 73 are interlocked with the inner tank 5, in other words, connects the first circular plate 61 to the second circular plate 62 through penetration, and in the disconnecting position II, the inner tank connecting pin 81 disconnects a connection between the sticks 73 and the inner tank 5, in other words, disconnects the first circular plate 61 from the second circular plate 62 without coming into contact with, engaging with, or penetrating through the first circular plate 61. In the connecting position I, the inner tank connecting pin 81 also rotates integrally with the first circular plate 61, the second circular plate 62, the sticks 73, and the inner tank 5. For the movement of the inner tank connecting pin 81, hand or a driving apparatus such as a straight advancing mechanism operated by a motor can be appropriately used.

The main body connecting pin 82 is supported in an erected manner on a supporting member 63 that is fixed to the apparatus main body 3, and moves downward from the supporting member 63 so as to engage with or penetrate through (simply referred to as "penetrate" hereinafter) the second circular plate 62. As a result, the main body connecting pin 82 can move between a fixing position III and a movable position IV through, for example, extraction and insertion in the vertical direction, where in the fixing position III, the main body connecting pin 32 connects the sticks 73 to the supporting member 63 so that the sticks 73 are fixed to the apparatus main body 3, in other words, connects the supporting member 63 to the second circular plate 62, and in the movable position IV, the main body connecting pin 82 disconnects a connection between the supporting member 63 and the second circular plate 62, in other words, disconnects the supporting member 63 from the second circular plate 62 without coming into contact with, engaging with, or penetrating through the second circular plate 62.

Therefore, the connecting shaft 80 and the shaft 13 share the rotation axis along the vertical direction, and through extraction and insertion of the inner tank connecting pin 81 of the second circular plate 62 with respect to the first circular plate 61, switching can be performed between a state in which the sticks 73 and the inner tank 5 rotate in an interlocking manner in the connecting position I, and a state in which the sticks 73 and inner tank 5 are disconnected from each other in the disconnecting position II. Moreover, through extraction and insertion, with respect to the second circular plate 62, of the main body connecting pin 82 of the supporting member 63 on a side of the apparatus main body 3, switching can be performed between a state in which the second circular plate 62 is fixed to the apparatus main body 3 in the fixing position III, and a state in which the second circular plate 62 is disconnected from the apparatus main body 3 in the movable position IV.

With the switching mechanism 60 described above, when the inner tank connecting pin 81 is inserted into the first circular plate 61 and the main body connecting pin 82 is extracted from the second circular plate 62, the first circular plate 61 and the second circular plate 62 can integrally rotate the inner tank 5 and the sticks 73 in an interlocking manner using the motor 12. On the other hand, when the inner tank connecting pin 81 is extracted from the first circular plate 61 arid the main body connecting pin 82 is inserted into the second circular plate 62, only the inner tank 5 can be rotated using the motor 12 while the sticks 73 are fixed to the apparatus main body 3.

An outer tank bottom 15 and an inner tank bottom 17 can be opened and closed around rotation axes of hinges 71 and 72 by the hinges 71 and 72 as an example of an opening and closing unit with respect to the outer tank 4 and the inner tank 5, respectively. The take-out unit 6 is disposed in a lower portion of the apparatus main body 3 below the outer tank bottom 15 and the inner tank bottom 17.

A processed paper diaper can be taken out from the take-out unit 6. Inside the take-out unit 6, the storage container 7 to which the disposal bag 8 is attached is placed. The disposal bag 8 is placed immediately below the inner tank bottom 17. By making an opening of the storage container 7 larger than an opening at a bottom of the inner tank 5, the processed paper diaper can be smoothly dropped into the disposal bag 8 of the storage container 7.

Figure 1B:
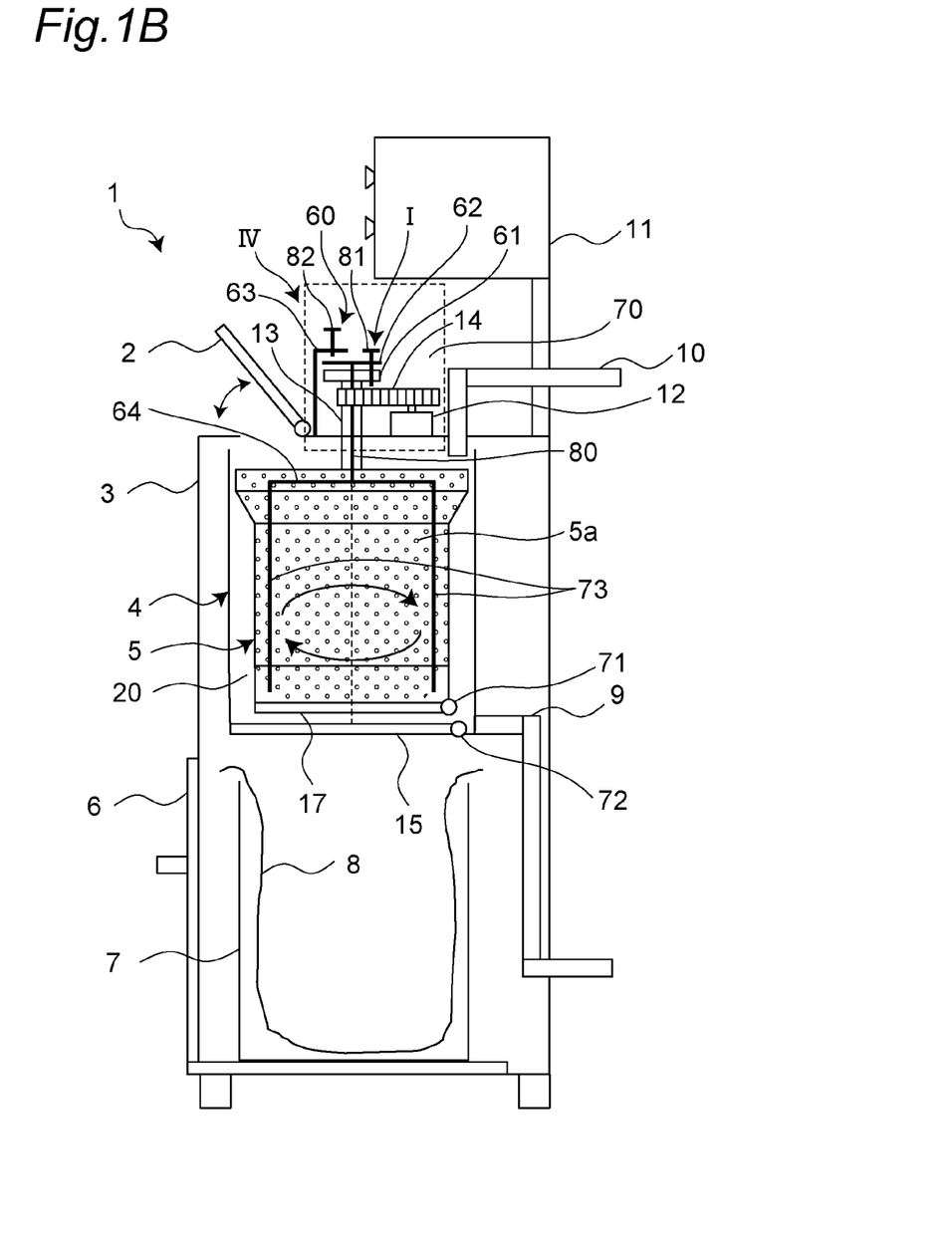
FIG. 1B is a side sectional view showing a configuration of the used paper diaper processing apparatus according to a modification of the first embodiment of the present disclosure.

As shown in FIG. 1B, the tapered portions 4d and 5d need not be attached to the lower portions of the outer tank 4 and inner tank 5. When the tapered portions 4d and 5d are attached, diameters of the outer tank bottom 15 and the inner; tank bottom 17 can be reduced, and a space necessary for opening and closing around the rotation axes of the hinges 71 and 72 by the hinges 71 and 72 can be reduced. As a result, an amount of processed diapers stored in the storage container 7 can be increased.

Operation

[Operation]

Next, processing operation of the used paper diaper processing apparatus 1 will be described. In the following, for convenience of explanation, a state in which stirring operation is performed after the used paper diaper 18 is inserted and placed in the inner tank 5 (FIG. 2), a state in which dehydration processing is performed through high-speed rotation of the inner tank 5 (FIG. 3A), and a state in which the outer tank bottom 15 and the inner tank bottom 17 are opened and operation of taking out the used paper diaper 18 after processing to the take-out unit 6 is performed (FIG. 5) will be described separately.

Figure 2:
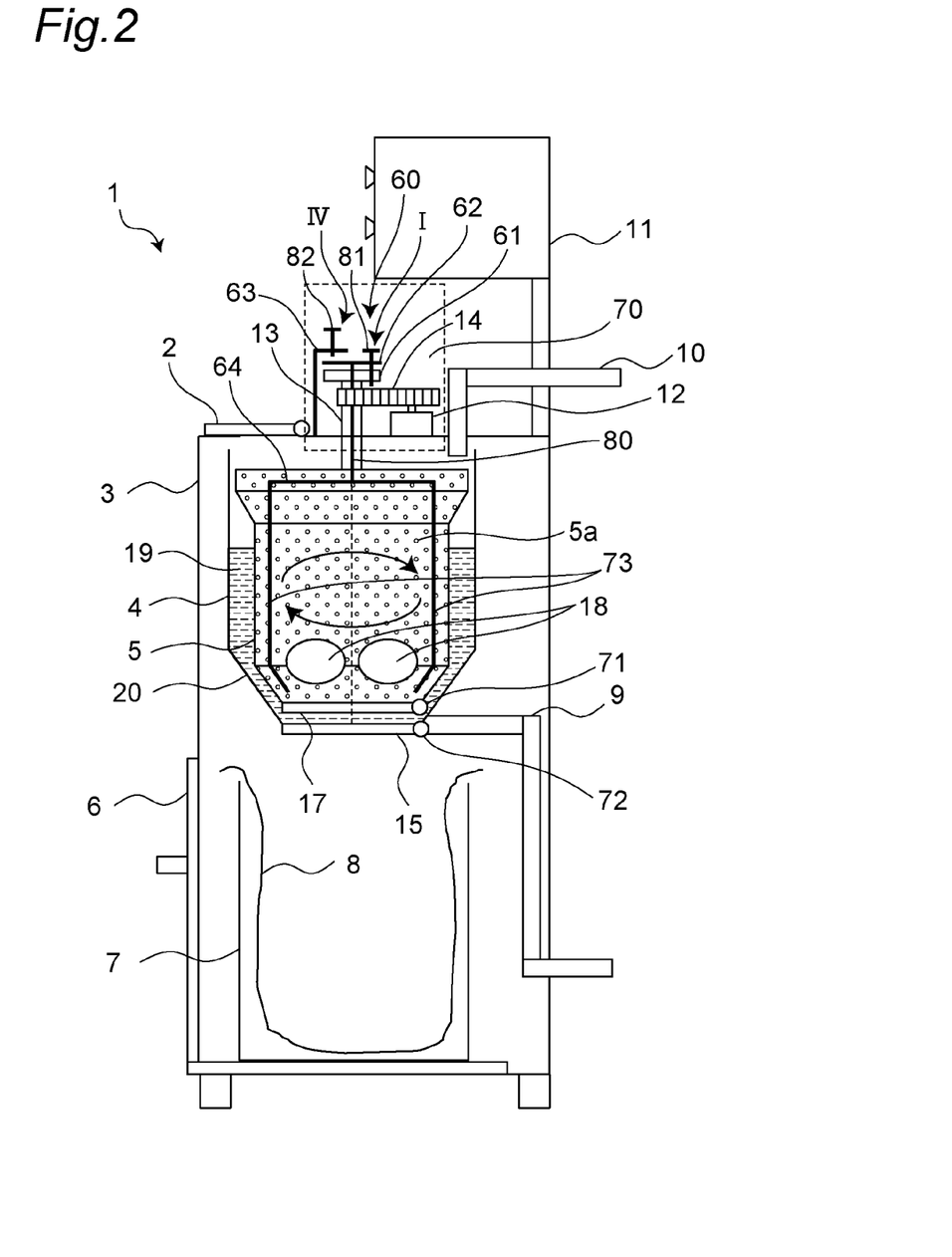
FIG. 2 is a side sectional view showing the used paper diaper processing apparatus in a state in which a used paper diaper is disposed in a processing tank and stirring operation is performed in the first embodiment of the present disclosure.

In FIG. 2, water is supplied from the liquid supply unit 10 into the processing tank 20 and a certain amount of water is stored in the processing tank 20. Further, while the inner tank connecting pin 81 of the second circular plate 62 is inserted into the first circular plate 61 and placed in the connecting position I and the second circular plate 62 is connected to the first circular plate 61, the main body connecting pin 82 is extracted from the second circular plate 62 and placed in the movable position IV and the second circular plate 62 is disconnected from the apparatus main body 3, as a result of which the inner tank 5 and the sticks 73 rotate in an interlocking manner.

Next, a chemical for lowering a water absorption function of a superabsorbent polymer la put from the liquid supply unit 10 into the processing tank 20 and mixed with the water already put in the processing tank 20. Accordingly, the processing liquid 19 is stored in the processing tank 20. As the chemical for lowering the water absorption function of the superabsorbent polymer, a substance containing metal ions is preferable, and especially, calcium chloride, lime, or the like containing a divalent metal can be used.

Next, the used paper diaper 18 is put into the inner tank 5 from the loading door 2, and the motor 12 is rotationally controlled under the control of the control apparatus 11 to execute stirring operation. Specifically, when the motor 12 rotates, the shaft 13 rotates via the belt 14, and the inner tank 5 rotates with respect to the outer tank 4. In this way, the processing liquid 19 and the used paper diaper 18 are stirred. When the stirring operation is continued for a while (as an example, preferably about 5 to 30 minutes), the superabsorbent polymer of the used paper diaper 18 and, for example, divalent metal ions in the chemical react with each other. Accordingly, water contained in the superabsorbent polymer is removed from the used paper diaper 18, and the removed water is mixed with the processing liquid 19, In the stirring operation here, the processing liquid 19 and the superabsorbent polymer of the used paper diaper 18 only need to react with each other. It is important to perform gentle stirring under the control of the control apparatus 11 so that the used paper diaper 18 is not separated and disassembled by the stirring operation. Specifically, the gentle stirring is preferably about 40 to 160 rpm, for example.

By inserting the used paper diaper 18 in a state in which the processing liquid 19 mixed with the chemical is stored in the processing tank 20, it is possible to prevent the used paper diaper 18 from expanding in the inner tank 5. If the used paper diaper 18 is inserted in a state in which only the water is stored and the processing liquid 19 containing the chemical is not stored, the superabsorbent polymer absorbs the water, and the used paper diaper 18 expands greatly. In this case, an issue in which the number of used paper diapers 18 that can be put into the inner tank 5 at a time is limited and an issue in which the inner tank 5 must be enlarged occur. On the other hand, when the processing liquid 19 mixed with the chemical is stored in the processing tank 20, the occurrence of these issues can be suppressed.

Figure 3A:
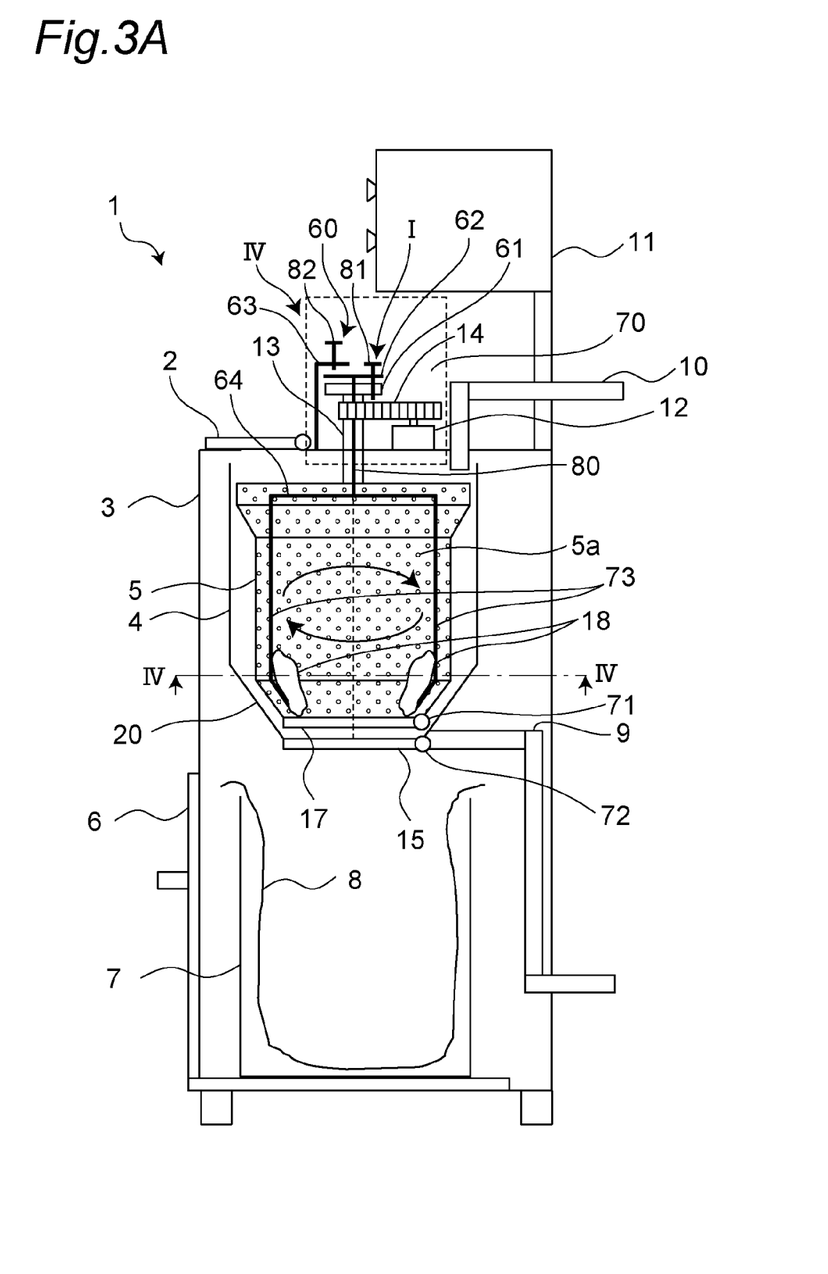
FIG. 3A is a side sectional view showing the used paper diaper processing apparatus in a state in which dehydration operation is performed through high-speed rotation of the inner tank in the first embodiment of the present disclosure.

Next, dehydration operation of the used paper diaper 18 will be described with reference to FIG. 3A. After the liquid such as the processing liquid accumulated in the outer tank 4 is drained from the liquid discharge unit 9, the inner tank 5 is rotated at a high speed with respect to the outer tank 4. As a result, the used paper diaper 18 can be dehydrated, and weight of the used paper diaper 18 can be reduced. Specifically, the stirring is preferably about 800 to 1300 rpm. At this time, the used paper diaper 18 is pressed outward in the inner tank 5 by centrifugal force. An adhesive may be used in the used paper diaper 18. When the processing operation is continuously performed, the dissolved adhesive may be attached to the inside of the inner tank 5, and due to the adhesive, the inner tank 5 and the used paper diaper 18 may be easily stuck together after dehydration. When the tapered portion 5d is provided in the lower portion of the inner tank 5, the used paper diaper 18 tends to stick particularly to the tapered portion 5d.

Figure 3B:
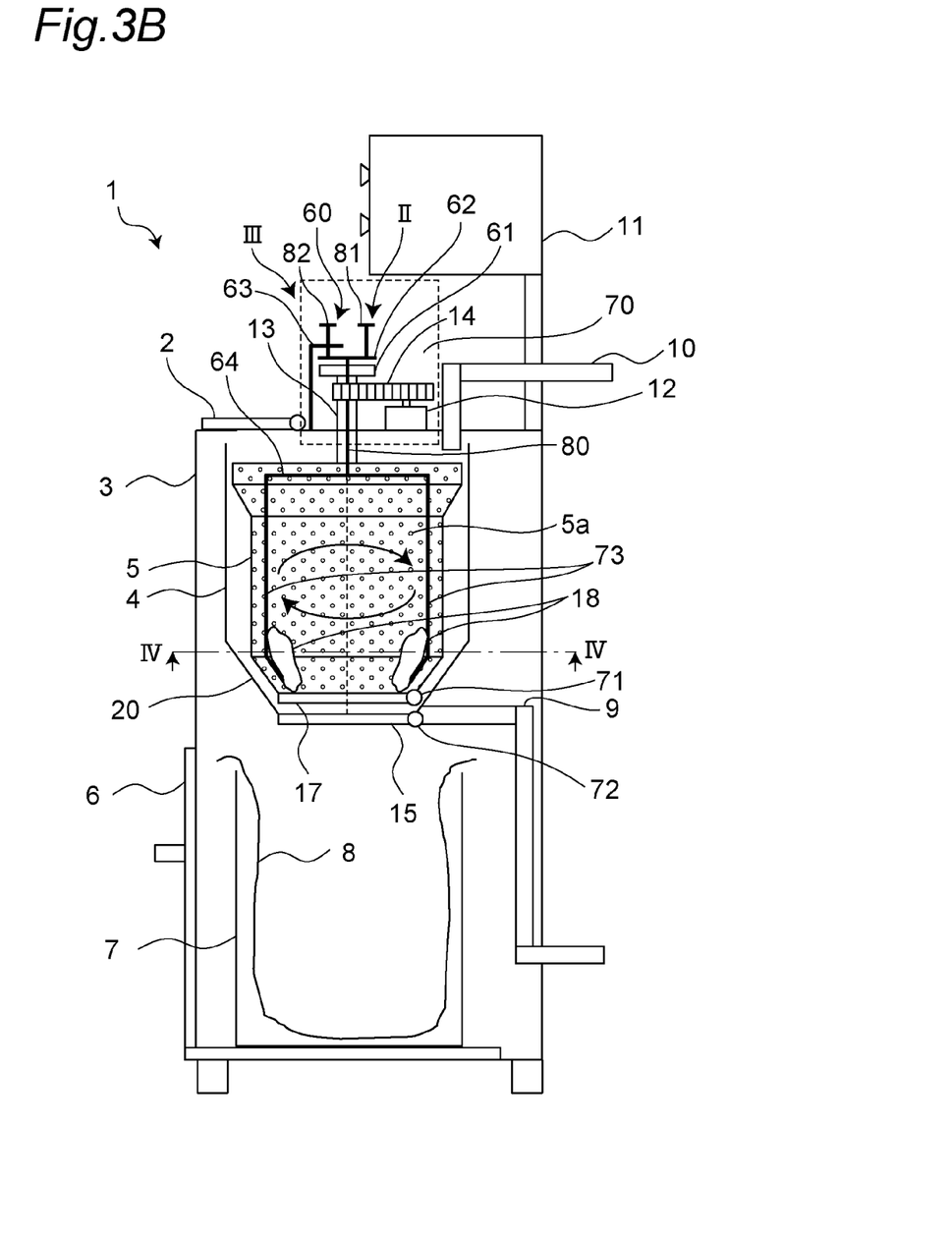
FIG. 3B is a side sectional view showing the used paper diaper processing apparatus in a state in which peeling operation is performed through rotation of the inner tank in the first embodiment of the present disclosure.
Figure 4A:
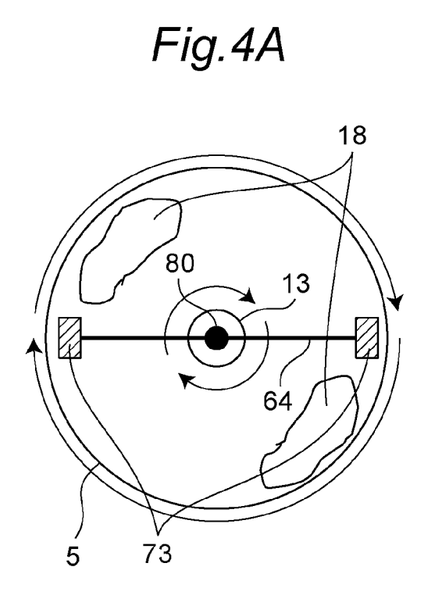
FIG. 4A is a sectional view cut along line IV-IV of FIG. 3A for explaining the dehydration processing operation.
Figure 4B:
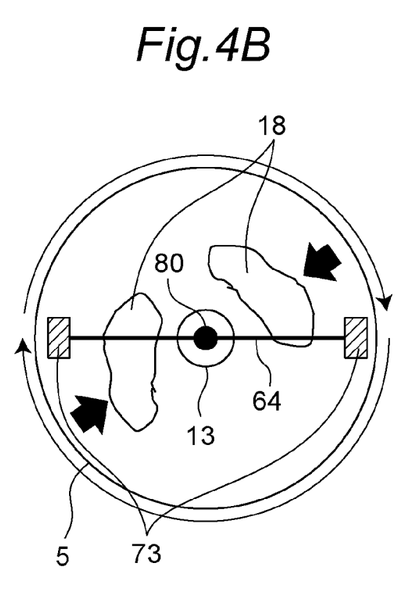
FIG. 4B is a sectional view cut along line IV-IV of FIG. 3B for explaining a case of performing the peeling operation, in the first, embodiment of the present disclosure.

Next, peeling operation of the used paper diaper 18 that, has been stuck to the inner tank 5 will be described with reference to FIG. 3B. In the operations thus far, since the inner tank connecting pin 81 is placed in the connecting position I while being inserted into the first circular plate 61, and the main body connecting pin 82 is placed in the movable position IV while being extracted from the second circular plate 62, the inner tank 5 and the sticks 73 rotate in an interlocking manner (see FIG. 4A), On the other hand, when the peeling operation is performed, the inner tank connecting pin 81 is placed in the disconnecting position II while being extracted from the first circular plate 61, and the main body connecting pin 82 is placed in the fixing position III while being inserted into the second circular plate 62. In such a state, the sticks 73 are disconnected from the inner tank 5 and the sticks 73 are connected to the apparatus main body 3. As a result, only the inner tank 5 rotates and the sticks 73 are fixed with respect to the inner tank 5 (see FIG. 4B). In this state, the inner tank 5 is rotated at a low speed of about 10 rpm, for example, using the motor 12, the used paper diaper 18 stuck to a side surface or the like of the inner tank 5 is caught on the fixed sticks 73 and peels off from the inner tank 5.

Figure 5:
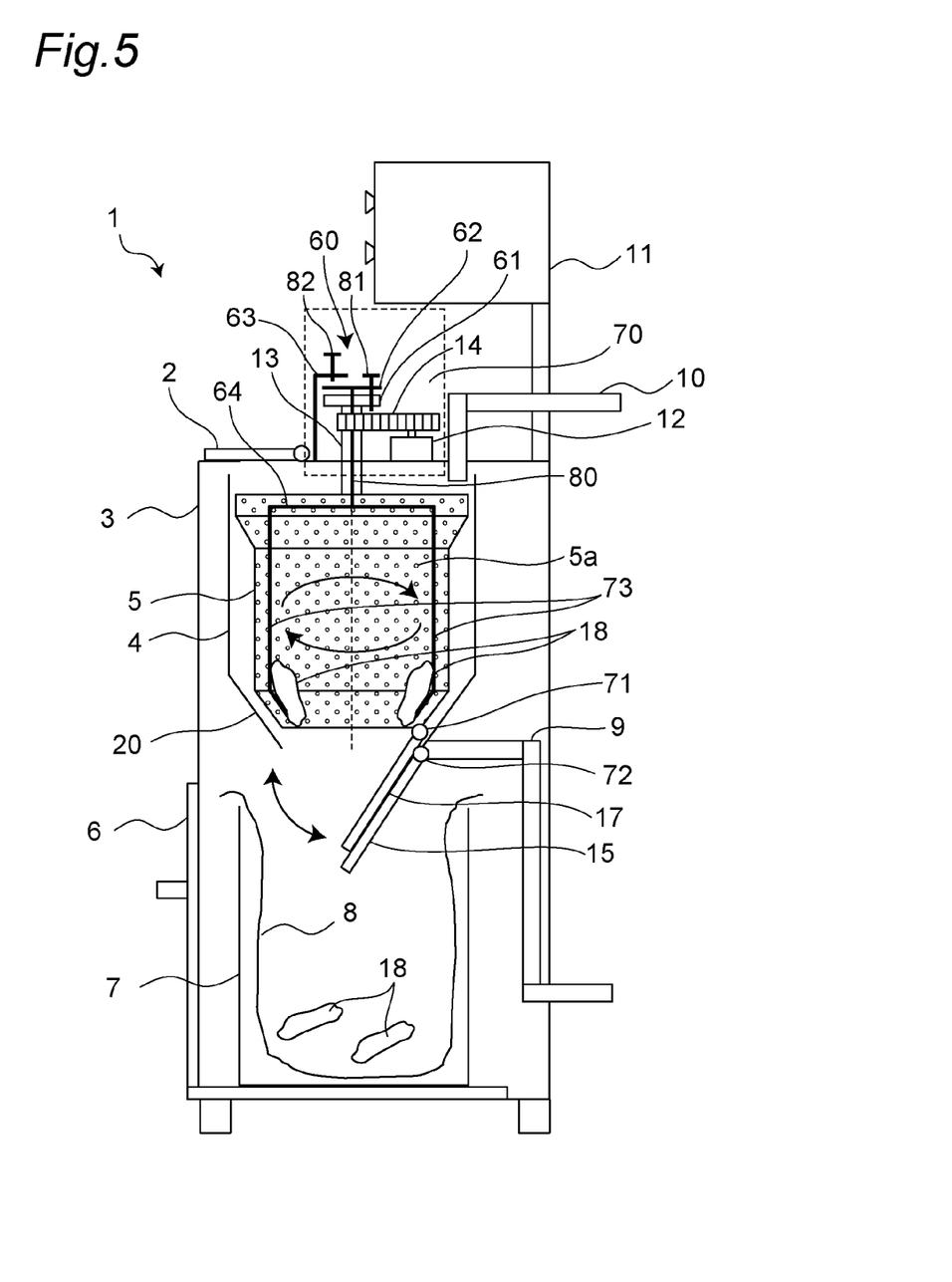
FIG. 5 is a side sectional view showing the used paper diaper processing apparatus in a state in which a bottom of the processing tank is opened and taking-out operation of the used paper diaper after processing is performed in the first embodiment of the present disclosure.

Next, taking-out operation of the used paper diaper 18 will be described with reference to FIG. 5. When the outer tank bottom 15 arid the inner tank bottom 17 are opened via the hinges 71 and 72 in a state in which the dehydration is finished, the used paper diaper 18 falls into the disposal bag 8 installed in the storage container 7. When the used paper diaper 18 is discharged, it can be discharged simply by taking out the take-out unit 6 from the apparatus main body 3 by sliding the take-out unit 6 laterally with respect to the apparatus main body 3, and taking out the disposal bag 8 from the storage container 7.

As described above, according to the first embodiment, the bottom of the outer tank 4 and the bottom of the inner tank 5 can be opened and closed, and the sticks 73 are disposed which are installed inside the inner tank and for which switching can be performed between the state of rotating in the interlocking manner with the inner tank 5 and the state of being disconnected from the inner tank 5. In this way, with the disconnected sticks 73, the used paper diaper 18 after dehydration can be peeled off from the side surface of the inner tank, the used paper diaper 18 after processing can be dropped and taken out from below, and it is possible to reduce work and hygiene burdens of an operator. Moreover, the used paper diaper 18 subjected to the weight reduction processing with the chemical containing metal ions or the like is not separated and disassembled in the processing tank 20, and a fiber portion thereof remains. Further, the used paper diaper 18 after processing does not need to be taken out directly by an operator from above the inner tank, and can be stored in the disposal bag 8 without bothering the operator. Therefore, work and hygiene burdens on the operator can be reduced.

Note that, in the first embodiment, the disposal bag 8 is installed in the storage container 7. However, the used paper diaper 18 may be directly stored in the storage container 7 without installing the disposal bag 8.

In addition, instead of preparing the processing liquid 19 by putting therein the chemical containing metal ions or the like after the water is stored in the processing tank 20, a processing liquid 19 in which water and a chemical are mixed may be prepared in advance, and the prepared processing liquid 19 may be directly stored in the processing tank 20.

Further, the inner tank 5 can be directly driven by the motor 12 without using the belt 14 to rotate the inner tank 5.

Further, although the sticks 73 are fixed and the inner tank 5 is rotated to perform the peeling operation, the same effect can be obtained in an opposite manner when the inner tank 5 is fixed and the sticks 73 are rotated.

Further, the number of sticks 73 may be at least one, and even when there is a plurality of the sticks 73, each of the sticks 73 exhibits the same effect.

Second Embodiment

Figure 6:
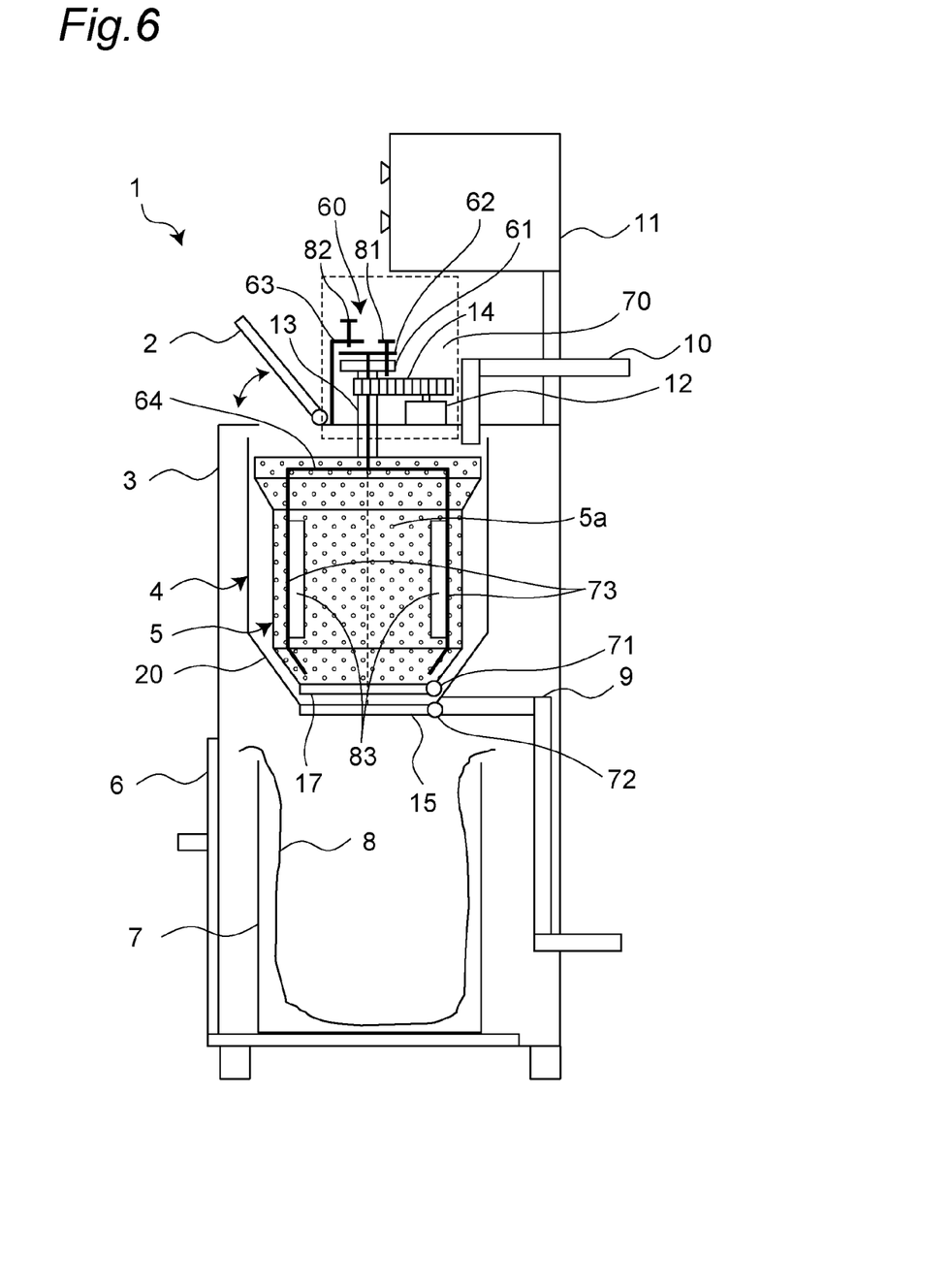
FIG. 6 is a side sectional view showing a configuration of a used paper diaper processing apparatus according to a second embodiment of the present disclosure.

FIG. 6 shows an apparatus configuration of a second embodiment, of the present disclosure.

In the first embodiment, the sticks 73 are simple sticks. However, when a blade 83 having a plate shape is attached to the stick 73 so as to extend in a direction orthogonal to a tangential direction of the inner tank 5, a water flow of stirring operation can be increased and processing time can be shortened. As a shape of the blade 83, for example, a rectangular plate is preferable so as to effectively generate a water flow.

FIG. 6 shows an apparatus configuration of a second embodiment of the present disclosure. Compared to the first embodiment, a difference is that the blade 83 is attached to a side surface of each of the sticks 73.

According to the configuration of the second embodiment, the blades 83 attached to the sticks 73 can generate a strong water flow during stirring operation and promote a stirring action. As a result, processing time required for stirring can be shortened. The blade 83 for increasing the water flow can also be attached to the side surface of the inner tank. However, in order for the fixed sticks 73 and the blade 83 attached to an internal side surface of the inner tank 5 not to interfere with each other during peeling operation, only a very small blade can be attached. Here, a very small blade means the following blade, for example. When a thickness of the diaper pressed against the side surface of the inner tank 5 is about 2 cm, for example, the sticks 73 are placed in positions about 1 cm away from the inner tank 5 toward a center side. At this time, in order for the sticks 73 and blade 83 not to interfere with each other, the blade 83 to be attached needs to be thin and less than 1 cm such as 0.9 cm.

As described above, according to the second embodiment, the blade 83 can generate a strong water flow and promote a stirring action, the processing can be completed in a shorter time, and when the inner tank 5 is rotated, the sticks 73 that are fixed and not rotated can peel off the used paper diaper 18 from the inner tank 5.

Although the embodiments of the present disclosure have been described above, the embodiments are only the illustration for implementing the present disclosure. Therefore, the present disclosure is not limited to the above-described embodiments, and can be implemented by appropriately modifying the embodiments without departing from the spirit thereof.

For example, by appropriately combining arbitrary embodiments or modifications of the above-described various embodiments or modifications, the respective effects can be produced. Moreover, a combination of embodiments, a combination of working examples, or a combination of an embodiment(s) and a working example(s) is possible, and a combination of characteristics in different embodiments or working examples is also possible.

The used paper diaper processing apparatus according to the above aspects of the present disclosure can lower a water absorption function of a superabsorbent polymer that absorbs water contained in excrement to remove water by mixing the superabsorbent polymer and a chemical containing divalent metal ions or the like, and can reduce weight by lowering an amount of water contained in the used paper diaper. Moreover, the used paper diaper processing apparatus according to the above aspects of the present disclosure does not require an operator to take out the used paper diaper after processing directly from the inner tank. Therefore, the apparatus can reduce work and hygiene burdens on the operator and can be used to improve work in an elderly facility or a childcare facility using a large amount of paper diapers.

Although the present disclosure has been fully described in connection with the embodiments thereof with reference to the accompanying drawings, it is to be noted that various changes and modifications are apparent to those skilled in the art. Such changes and modifications are to be understood as included within the scope of the present, disclosure as defined by the appended claims unless they depart therefrom.

What is claimed is:

1. A used paper diaper processing apparatus, comprising:
   a processing tank that processes a used paper diaper;
   a liquid supply unit that supplies a processing liquid to the processing tank;
   a liquid discharge unit that discharges the processing liquid from the processing tank; and
   a take-out unit that takes out a paper diaper processed in the processing tank below the processing tank,
   wherein the processing tank has:
   an inner tank having a cylindrical shape that stores the used paper diaper and has a plurality of through holes smaller than the paper diaper on at least either a side surface thereof or a bottom surface thereof, and an outer tank that surrounds the side surface and the bottom surface of the inner tank;
   at least one peeling member inside the inner tank;
   a switching mechanism that performs switching between a state in which the peeling member and the inner tank rotate in an interlocking manner and a state in which the peeling member is disconnected from the inner tank,
   the used paper diaper processing apparatus further comprising:
   a rotation drive unit that rotates the inner tank or the peeling member around an axis of the inner tank; and
   an opening and closing unit that discharges the paper diaper processed in the processing Lank from a bottom of the processing tank to the take-out unit.

2. The used paper diaper processing apparatus according to claim 1, wherein a blade is attached to the peeling member, the blade extending in a direction orthogonal to a tangential direction of the cylindrical shape of the inner tank.

3. The used paper diaper processing apparatus according to claim 1, wherein
   the switching mechanism includes:
   a first connecting member that is movable between a connecting position in which the first connecting member connects the peeling member to the inner tank such that the peeling member and the inner tank interlock with each other and a disconnecting position in which the first connecting member disconnects a connection between the peeling member and the inner tank; and
   a second connecting member that is movable between a fixing position in which the second connecting member connects and fixes the peeling member to a processing apparatus main body and a movable position in which the second connecting member disconnects a connection of the peeling member to the processing apparatus main body to allow the peeling member to be movable.

4. The used paper diaper processing apparatus according to claim 2, wherein
   the switching mechanism includes:
   a first connecting member that is movable between a connecting position in which the first connecting member connects the peeling member to the inner tank such that the peeling member and the inner tank interlock with each other and a disconnecting position In which the first connecting member disconnects a connection between the peeling member and the inner tank; and
   a second connecting member that is movable between a fixing position in which the second connecting member connects and fixes the peeling member to a processing apparatus main body and a movable position in which the second connecting member disconnects a connection of the peeling member to the processing apparatus main body to allow the peeling member to be movable.

* * * * *

UNITED STATES PATENT AND TRADEMARK OFFICE
CERTIFICATE OF CORRECTION

PATENT NO. : 11,731,177 B2
APPLICATION NO. : 17/024025
DATED : August 22, 2023
INVENTOR(S) : Genichiro Matsuda et al.

It is certified that error appears in the above-identified patent and that said Letters Patent is hereby corrected as shown below:

On the Title Page

In item (73) Assignee: replace "PANASONIC CORPORATION, Osaka (JP)" with -- PANASONIC HOLDINGS CORPORATION, Osaka (JP) --.

Signed and Sealed this
Eleventh Day of June, 2024

Katherine Kelly Vidal
*Director of the United States Patent and Trademark Office*